(12) United States Patent
Lopez et al.

(10) Patent No.: US 8,590,364 B2
(45) Date of Patent: Nov. 26, 2013

(54) BEVERAGE DISGUISE FOR HAND HELD BREATHALYZER INTERFACE OF IGNITION INTERLOCK DEVICE

(76) Inventors: Davin E. Lopez, Las Cruces, NM (US); Luis M. Ortiz, Albuquerque, NM (US)

( * ) Notice: Subject to any disclaimer, the term of this patent is extended or adjusted under 35 U.S.C. 154(b) by 383 days.

(21) Appl. No.: 13/100,424

(22) Filed: May 4, 2011

(65) Prior Publication Data

US 2012/0031166 A1    Feb. 9, 2012

Related U.S. Application Data

(60) Provisional application No. 61/370,282, filed on Aug. 3, 2010.

(51) Int. Cl.
    *G01N 33/497*    (2006.01)
(52) U.S. Cl.
    USPC .......................................... 73/23.3; 180/272
(58) Field of Classification Search
    USPC .......................................... 73/23.3; 180/272
    See application file for complete search history.

(56) References Cited

U.S. PATENT DOCUMENTS

| | | | | |
|---|---|---|---|---|
| 4,749,553 | A * | 6/1988 | Lopez et al. ................ | 422/84 |
| 5,020,628 | A | 6/1991 | Bigliardi et al. ............. | 180/272 |
| 5,065,604 | A | 11/1991 | Pattock ........................ | 70/239 |
| 6,229,908 | B1 | 5/2001 | Edmonds, III et al. ...... | 382/124 |
| 6,853,956 | B2 | 2/2005 | Ballard, Jr. et al. .......... | 702/183 |
| 7,204,335 | B2 * | 4/2007 | Stewart et al. ............... | 180/272 |
| 7,287,617 | B2 | 10/2007 | Mobley et al. ............... | 180/272 |
| 7,341,693 | B2 | 3/2008 | Der Ghazarian et al. ..... | 422/84 |
| 7,413,047 | B2 | 8/2008 | Brown et al. ................ | 180/272 |
| 7,451,852 | B2 * | 11/2008 | Stewart et al. ............... | 180/272 |
| 7,797,982 | B2 | 9/2010 | Burke et al. ................. | 73/23.3 |
| 8,336,665 | B1 * | 12/2012 | Saunders .................... | 180/272 |
| 8,418,796 | B2 * | 4/2013 | Flores ........................ | 180/272 |
| 2007/0144812 | A1 * | 6/2007 | Stewart et al. ............... | 180/272 |
| 2007/0273537 | A1 | 11/2007 | Crespo et al. ............... | 340/576 |
| 2010/0012417 | A1 | 1/2010 | Walter et al. ................ | 180/272 |
| 2010/0063408 | A1 | 3/2010 | Nothacker et al. ........... | 600/532 |
| 2011/0084820 | A1 | 4/2011 | Walter et al. ............ | 340/426.24 |
| 2012/0234708 | A1 * | 9/2012 | Chabot ....................... | 206/320 |
| 2013/0062232 | A1 * | 3/2013 | Saunders .................... | 206/305 |

OTHER PUBLICATIONS

Breathalyzer; Wikipedia; http://en.wikipedia.org/wiki/Breathalyzer.

(Continued)

*Primary Examiner* — Hezron E Williams
*Assistant Examiner* — Rodney T Frank
(74) *Attorney, Agent, or Firm* — Luis M. Ortiz; Kermit D. Lopez; Ortiz & Lopez, PLLC (57) ABSTRACT

A breath alcohol ignition interlock device includes a mock beverage housing including at least one of breath alcohol electronics and a hand held breath alcohol analyzer therein, a mouthpiece in fluid communication with an alcohol sensor associated with the at least one of breath alcohol electronics and a hand held breath alcohol analyzer and a vent exhausting breath from the mock beverage housing. The mock beverage container housing can be disguised as a coffee cup, a fountain drink cup, a soda can and a soft drink bottle. The mouthpiece can be disguised as a coffee cup lid, a fountain drink cup straw, a soda can opening and a soft drink bottle top. A wireless communication module can support data synchronization and communications between the device and a base station installed within a motor vehicle.

14 Claims, 7 Drawing Sheets

(56) References Cited

OTHER PUBLICATIONS

Taylor, Lawrence; State of the Art Breathalyzers: A History http://www.azduiatty.com/stateof-the-art-breathalyzers-a-history.htm.

Ignition Interlock Device; Wikipedia; http://en.wikipedia.org/wiki/ignition_interlock_device.
In-Horn-Your Alcohol Monitoring Alternative; http://www.smartstartinc.com/.

* cited by examiner

BEVERAGE DISGUISE FOR HAND HELD BREATHALYZER INTERFACE OF IGNITION INTERLOCK DEVICE

CROSS-REFERENCE TO PROVISIONAL APPLICATION

This patent application claims the benefit under 35 U.S.C. §119(e) of U.S. Provisional Application Ser. No. 61/370,282 entitled, "Beverage Disguise for Hand Held Breathalyzer Interface of Ignition Interlock Device," which was filed on Aug. 3, 2010 and is incorporated herein by reference in its entirety.

TECHNICAL FIELD

Embodiments are related to alcohol breathalyzers and ignition interlock systems. More particularly, embodiments are related to a disguise in the form of a mock non-alcoholic beverage (e.g., coffee cup, soda can, bottle soft drink) designed to accept the hand held breath analyzer therein and thereby disguising the hand held breath analyzer.

BACKGROUND

An ignition interlock device or a breath alcohol ignition interlock device (IID and BUD) is a breathalyzer installed on or around the dashboard of a vehicle, often as required by law following a DUI conviction. The ignition interlock device prevents a vehicle from starting until the driver successfully passes a blood alcohol concentration test. Before the vehicle will start, the driver must blow into the BAC tester. If the breath test shows a driver's BAC to be above a set limit, usually around 0.02-0.04%, the starter on the car vehicle will lock and the driver can't use the vehicle. If a driver's BAC is below that level, then the vehicle will start and operate normally.

IIDs are often issued as part of the mandatory punishment for a DUI/DWI conviction. A single DUI conviction could require that one of these systems be installed in the offender's car. If required by the court of law as part of a conviction or plea bargain, the DUI offender will also be responsible for paying for the installation and monthly usage fees for the devices, which may cost you hundreds of dollars. Alcohol detection devices can also include a camera to record the user of the system during its use and ensure that a driver is using the system. Wireless (cellular) reporting to remote monitoring stations is also being promoted and suggested for state adoption by breathalyzer system manufacturing companies.

Although breathalyzer systems can ensure public safety and deter future offenses by DUI offenders, their installation, albeit temporary, is unsightly and can be embarrassing to offenders. Many DUI offenders feel remorseful about the offense, willingly comply with terms of conviction or a plea that includes breathalyzer use and are otherwise law-abiding citizens. Compliance with breathalyzer usage to ensure sober vehicle operation is the only written purpose by states and municipality that legally require the installation of such systems in offender vehicles. Public embarrassment of offenders (especially first offenders), however, is not affirmatively written into legislation for jurisdictions mandating the use of breathalyzer systems.

For the foregoing reasons, the present inventor believes that DUI offenders that are required to pay for the installation and use of ignition interlock devices should also be able to disguise the user interface portion of such systems during a court-mandated period of use.

BRIEF SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

The present inventor proposes a disguise in the form of a mock non-alcoholic beverage (e.g., coffee cup, soda can, soft drink bottle) designed to hold at least one of integrated breath analyzer electronics or a hand held breath analyzer therein, thereby disguising the hand held breath analyzer as a beverage. The disguise can also be referred to herein for convenience as "breathalyzer disguise".

In accordance with an aspect of the disclosed embodiments, the breathalyzer disguise is provided as a mock beverage container such as a disposable coffee cup, fountain beverage cup, soda can or soft drink bottle that can accept and hold a hand held interface of a breathalyzer ignition interlock system therein.

In accordance with another aspect of the disclosed embodiments, the breathalyzer disguise can include a mouthpiece in fluid connection with a breath capture/input of a handheld interface for a breathalyzer ignition interlock system to accept breath from a user for analysis by the breathalyzer ignition interlock system.

In accordance with yet another aspect of the disclosed embodiments, the breathalyzer disguise can include exhaust vents therein allowing analyzed breath exiting the hand held interface of a breathalyzer ignition interlock interface to exit.

In accordance with another aspect of the disclosed embodiments, the breathalyzer disguise can be provided in a clamshell format to accept a hand held interface of a breathalyzer ignition interlock system.

In accordance with another aspect of the disclosed embodiments, a breathalyzer ignition interlock system can be provided with wireless communication capability and be provided in the form of a mock beverage container disguise.

In accordance with another aspect of the disclosed embodiments, a wireless breathalyzer ignition interlock system disguised as a beverage container can communicate with a base station installed within a motor vehicle.

In accordance with another aspect of the disclosed embodiments, a wireless breathalyzer ignition interlock system disguised as a beverage container can communicate with a base station installed within a motor vehicle using Bluetooth wireless communications.

In accordance with another aspect of the disclosed embodiments, a wireless breathalyzer ignition interlock system disguised as a beverage container can be synchronized with and can communicate with an assigned base station installed within a motor vehicle.

In accordance with another aspect of the disclosed embodiments, a wireless breathalyzer ignition interlock system disguised as a beverage container can be synchronized with and can communicate with an assigned base station installed within a motor vehicle using Bluetooth wireless communications.

The aforementioned aspects and other objectives and advantages can now be achieved as described herein. A breath alcohol ignition interlock device can comprise a mock beverage housing including at least one of breath alcohol electronics and a hand held breath alcohol analyzer therein, a mouthpiece in fluid communication with an alcohol sensor associated with the at least one of breath alcohol electronics and a hand held breath alcohol analyzer, and a vent exhausting breath from the mock beverage housing.

In another embodiment, the mock beverage container housing can be provided in the disguise of at least one of, for example, a coffee cup, a fountain drink cup, a soda can, a soft drink bottle, and so forth, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top.

In yet another embodiment, the mock beverage container housing accepts and holds therein a hand held interface of a breathalyzer ignition interlock device. In still another embodiment, the mock beverage container housing can be provided in the disguise of at least one of, for example, a coffee cup, a fountain drink cup, a soda can, a soft drink bottle, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top.

In other embodiments, the mouthpiece can be in fluid connection with a second mouthpiece associated with said handheld interface of a breathalyzer ignition interlock device.

In still other embodiments, the exhaust allows analyzed breath exiting the hand held interface of a breathalyzer ignition interlock interface to exit.

In still other embodiments, the mouthpiece can be in fluid connection with a second mouthpiece associated with said handheld interface of a breathalyzer ignition interlock device.

In another embodiment, the exhaust allows analyzed breath exiting the hand held interface of a breathalyzer ignition interlock interface to exit. In another embodiment, a wireless communication module can support communication with a base station installed within a motor vehicle.

In still another embodiment, the wireless communication module can comprise a Bluetooth wireless communications module.

In still further embodiments, the Bluetooth wireless communications module can support data synchronization and communications with said base station.

BRIEF DESCRIPTION OF THE DRAWINGS

The accompanying figures, in which like reference numerals refer to identical or functionally similar elements throughout the separate views and which are incorporated in and form a part of the specification, further illustrate the disclosed embodiments and, together with the detailed description herein, serve to explain the principles of the disclosed embodiments.

DETAILED DESCRIPTION

The particular values and configurations discussed in these non-limiting examples can be varied and are cited merely to illustrate one or more embodiments and are not intended to limit the scope thereof.

A beverage disguise for hand held breathalyzer interface of ignition interlock system can be provided in the form of a non-alcoholic beverage container. The non-alcoholic beverage container can be provided in the form of a mock, disposable coffee cup, paper cup, and soda can or soft drink bottle.

Figures 1, 2:
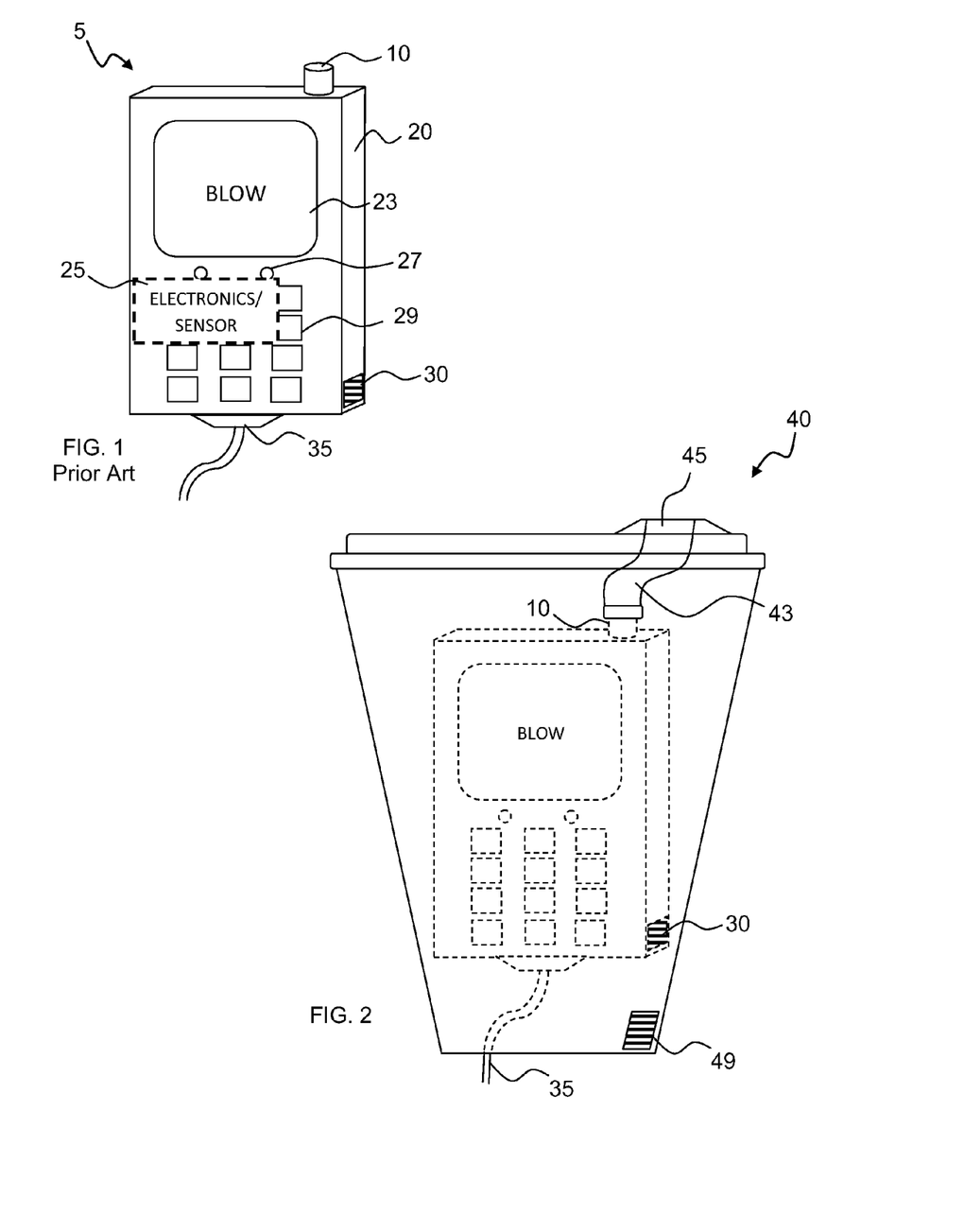
FIG. 1 labeled as "prior art" illustrates a hand held interface of a typical IID.
FIG. 2 illustrates a IID housing disguise in the form of a beverage container, in accordance with the disclosed embodiments.

Referring to FIG. 1, which is labeled as "prior art", a hand held user interface 5 of a typical breathalyzer and ignition interlock system is illustrated. The hand held user interface 5 includes a mouthpiece 10, a housing 20 connected to the mouthpiece 10 to accept user breath, a display screen 22, status indicator lights 27, alcohol analyzing electronics and sensors 25 to analyze user breath alcohol content, a vent 30 to exhaust user breath passing through the housing 20 for analysis, and wired connection 35 to an control module 37 (e.g., vehicle base station) installed within a motor vehicle for controlling vehicle ignition.

Modern ignition interlock devices use an ethanol-specific fuel cell for a sensor. A fuel cell sensor is an electrochemical device in which alcohol undergoes a chemical oxidation reaction at a catalytic electrode surface (platinum) to generate an Electric current. This current is then measured and converted to an alcohol equivalent reading. Although fuel cell technology is not as accurate or reliable as infrared spectroscopy technology used in evidentiary breathalyzers, they are cheaper and tend to be more specific for alcohol. The devices keep a record of the activity on the device and the interlocked vehicle's electrical system. This record, or log, is printed out or downloaded each time the device's sensors are calibrated, commonly at 30, 60, or 90-day intervals. Authorities may require periodic review of the log. If violations are detected, then additional sanctions can be implemented. Periodic calibration is performed using either a pressurized alcohol-gas mixture at a known alcohol concentration, or with an alcohol wet bath arrangement that contains a known alcohol solution.

The costs of installation, maintenance and calibration are generally paid by the offender, and typically are about $75 per month. In the United States, the National Highway Traffic Safety Administration's NHTSA Conforming Products List maintains a list of federally approved IID devices. Many countries are requiring the ignition interlock as a penalty for drivers convicted of driving under the influence, especially repeat offenders. Most U.S. states now permit judges to order the installation of an IID as a condition of probation; for repeat offenders, and for first offenders in some states, law may mandate installation.

FIG. 2 illustrates an IID housing disguise 40 provided in the form of a beverage container. The IID housing disguise 40 can accept the hand held user interface 5 of an IID. The IID housing disguise 40 includes a IID housing disguise mouthpiece interface 45 and a IID housing disguise vent 49. The IID housing disguise mouthpiece interface 45 can be placed in fluid connection 43 to a mouthpiece 10 of a hand held user interface 5. The IID housing disguise vent 49 can allow breath exhausted from the vent 30 of the hand held interface contained in the IID housing disguise 40 to also exhaust from the IID housing disguise 40. Wired connection 35 can also be achieved through an open bottom of the IID housing disguise 40.

Figure 3:
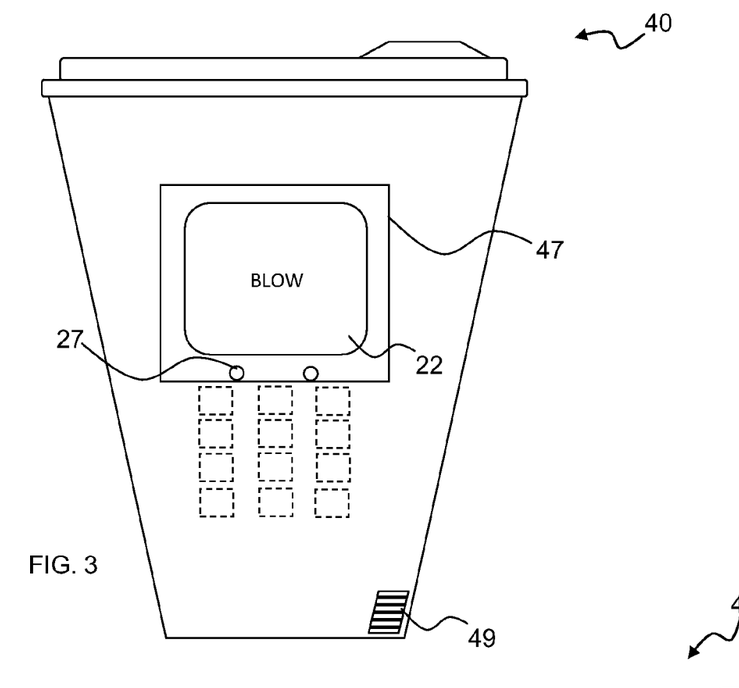
FIG. 3 illustrates an IID housing disguise holding/containing the hand held user interface of an IID therein and including a window cut into the side of IID housing disguise to allow users to see the display screen and status indicator lights disposed on the enclosed hand held user interface, in accordance with the disclosed embodiments.

FIG. 3 illustrates an IID housing disguise 40 holding/containing the hand held user interface 5 of an IID 20 therein and including a window 47 cut into the side of IID housing disguise 40 to allow users to see the display screen 22 and status indicator lights 27 disposed on the enclosed hand held user interface 5.

Figure 4:
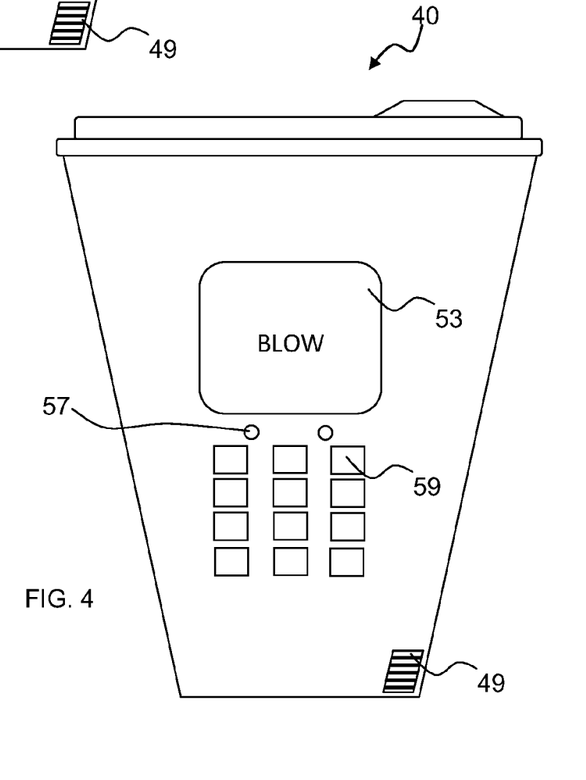
FIG. 4 illustrates an IID housing disguise holding/containing breath analyzing functionality of an IID therein and including a display screen and status indicator lights integrated into the side of IID housing disguise to allow users to see the commands on the display screen and of status indicator lights disposed on the IID housing, in accordance with the disclosed embodiments.

FIG. 4 illustrates an IID housing disguise 40 holding/containing breath analyzing functionality of an IID 20 therein and including a display screen 53 and status indicator lights 57 integrated into the side of IID housing disguise 40 to allow users to see the commands on the display screen 53 and of status indicator lights 57 disposed on the IID housing 40. A user interface 59 can also be integrated into the side of IID housing 40 to allow a user to operate the IID.

Figure 5:
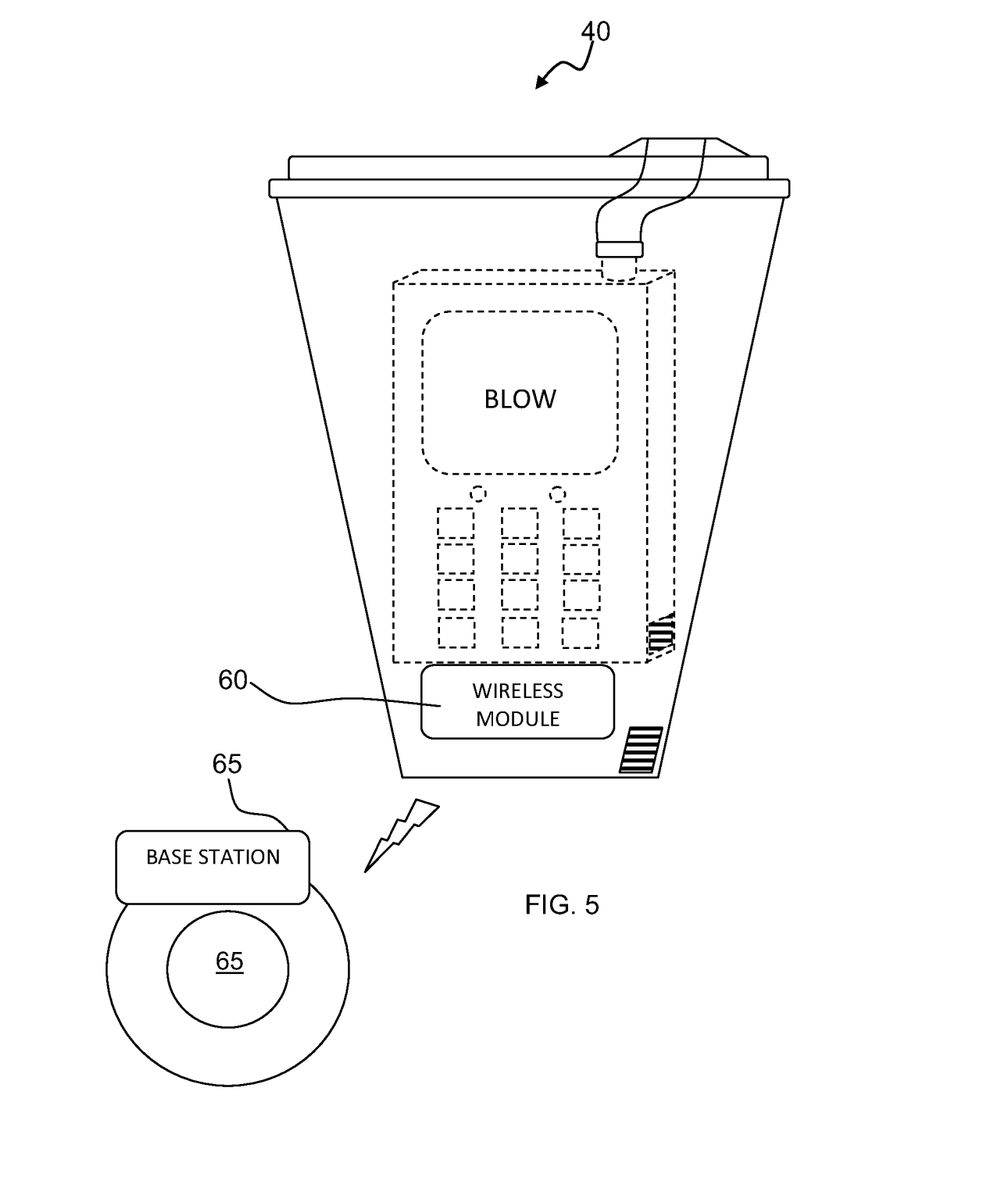
FIG. 5 illustrates an IID housing disguise is including a wireless communications module, in accordance with the disclosed embodiments.

It should be appreciated that communications can be maintained between the IID 40 and a base station 65 using wired communications 35 or wireless communications 60. Referring to FIG. 5, an IID housing disguise 40 is illustrated that includes a wireless communications module 60. Wireless communication module 60 can support wireless communication with a base station 65 installed within a motor vehicle associated with the IID 40. The wireless communication module 60 can be a Bluetooth wireless communications module to support data synchronization and communications between the IID 40 and the base station 65.

Figure 6:
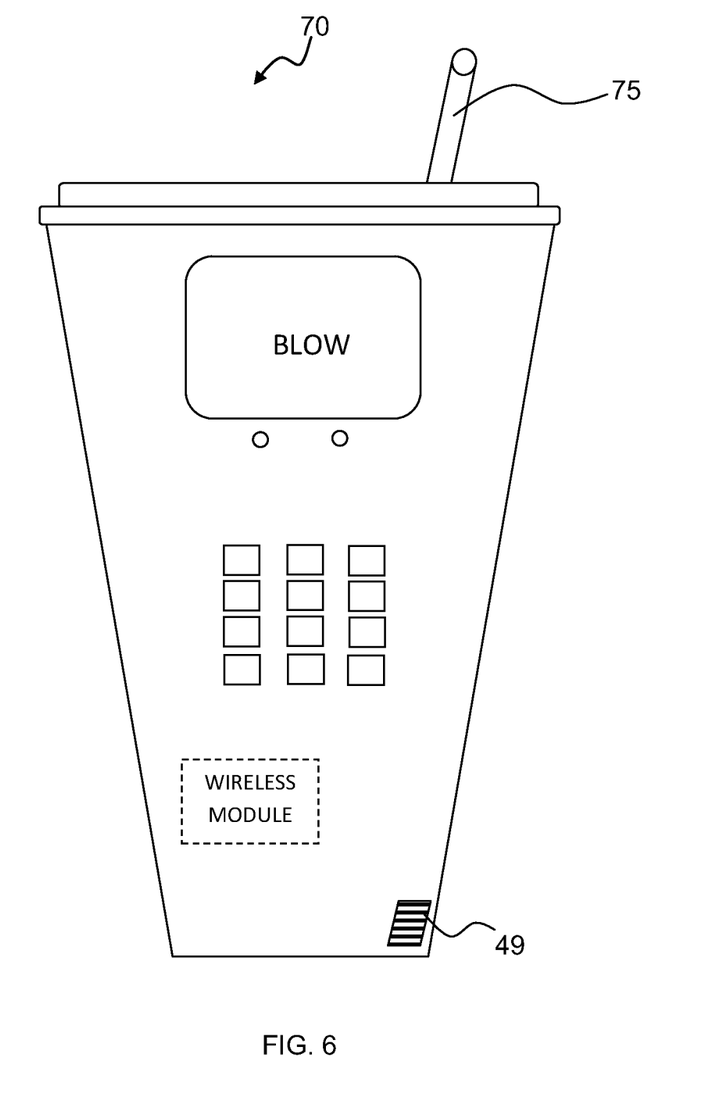
FIG. 6 illustrates an IID provided in the form of a beverage cup that includes a straw as the IID mouthpiece, in accordance with the disclosed embodiments.

FIG. 6 illustrates an IID 70 provided in the form of a beverage cup that includes a straw 70 as the IID mouthpiece. The straw 75 can be used by a user to blow into the IID 70. As also explained in FIG. 2, it should be appreciated that the straw 75 can be placed into fluid communication with mouthpiece 10 on an IID 40 that is being held within the IID 70. The IID 70 can also include a vent 49 for the exhaust of breath that is placed into the device by straw 75.

Figure 7:
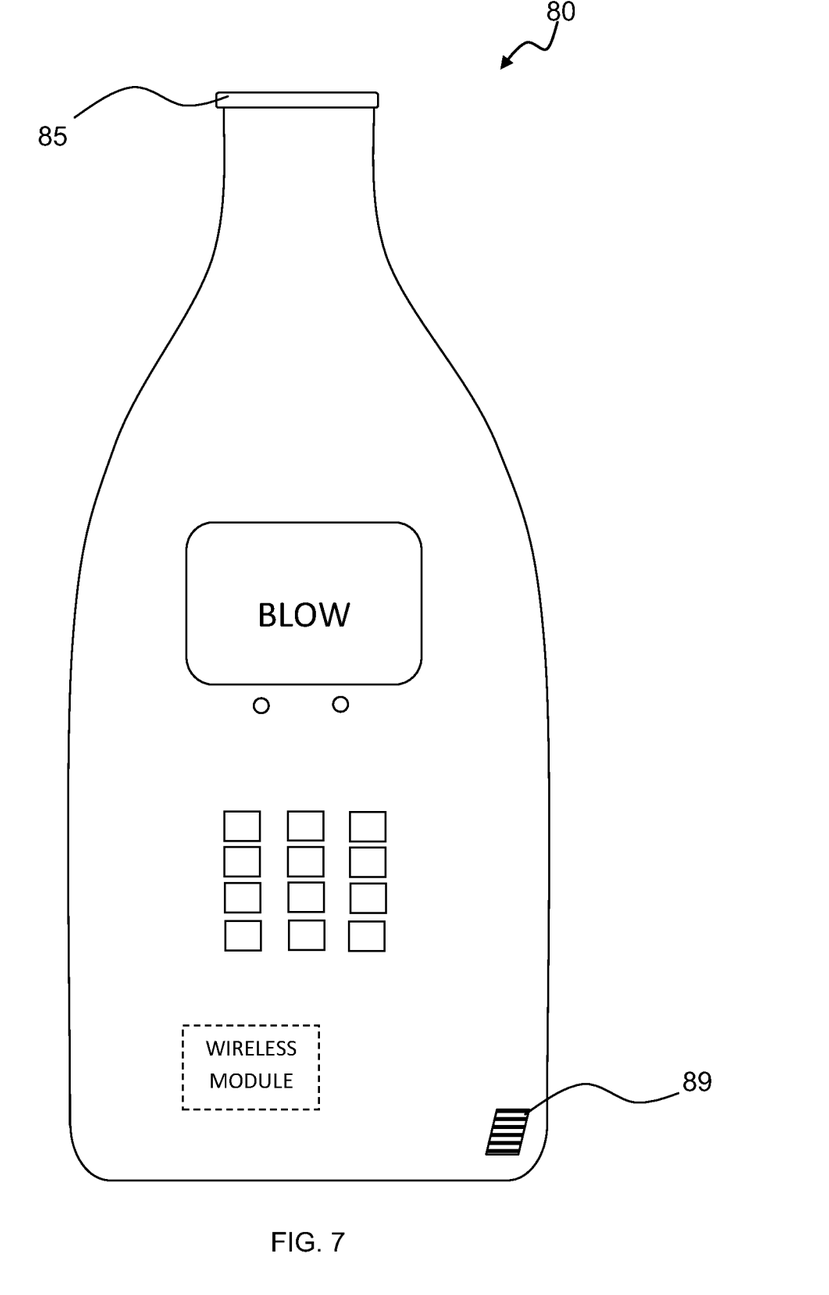
FIG. 7 illustrates an IID provided in the form of a beverage bottle that includes an opening as the IID mouthpiece, in accordance with the disclosed embodiments.

FIG. 7 illustrates an IID 80 provided in the form of a beverage bottle that includes an opening 85 as the IID mouthpiece. The opening 85 can be used by a user to blow into the IID 80. As also explained in FIGS. 2 and 6, it should be appreciated that the opening 85 can be placed into fluid communication with a mouthpiece 10 that can be carried inside the bottle-like IID 80. The IID 80 can also include a vent 89 for the exhaust of breath that is placed into the device by opening 85.

Figure 8:
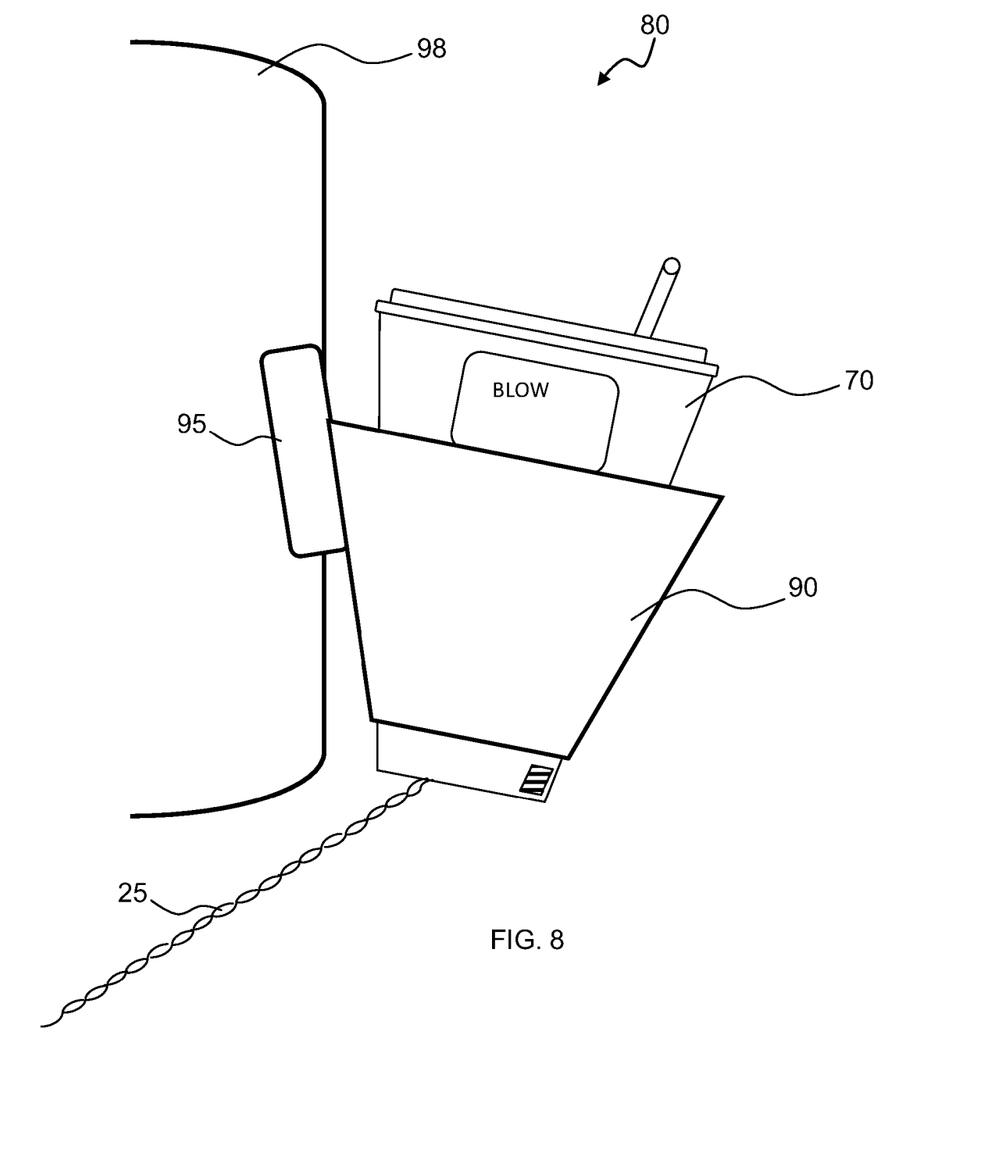
FIG. 8 illustrates a cup holder that can be provided to hold/support an IID beverage-housing disguise, in accordance with the disclosed embodiments.

FIG. 8 illustrates a cup holder 90 that can be provided to hold/support an IID beverage-housing disguise 70. The cup holder 90 can be mounted at a base 95 to a dashboard 98 of an associated motor vehicle. The cup holder 90 can safely hold an IID 70 while it is not in use. When used, wiring 25 is shown connecting the IID 70 with a base station mounted to a vehicle. Otherwise, communications with a base station can be wireless as described in detail above.

Figure 9:
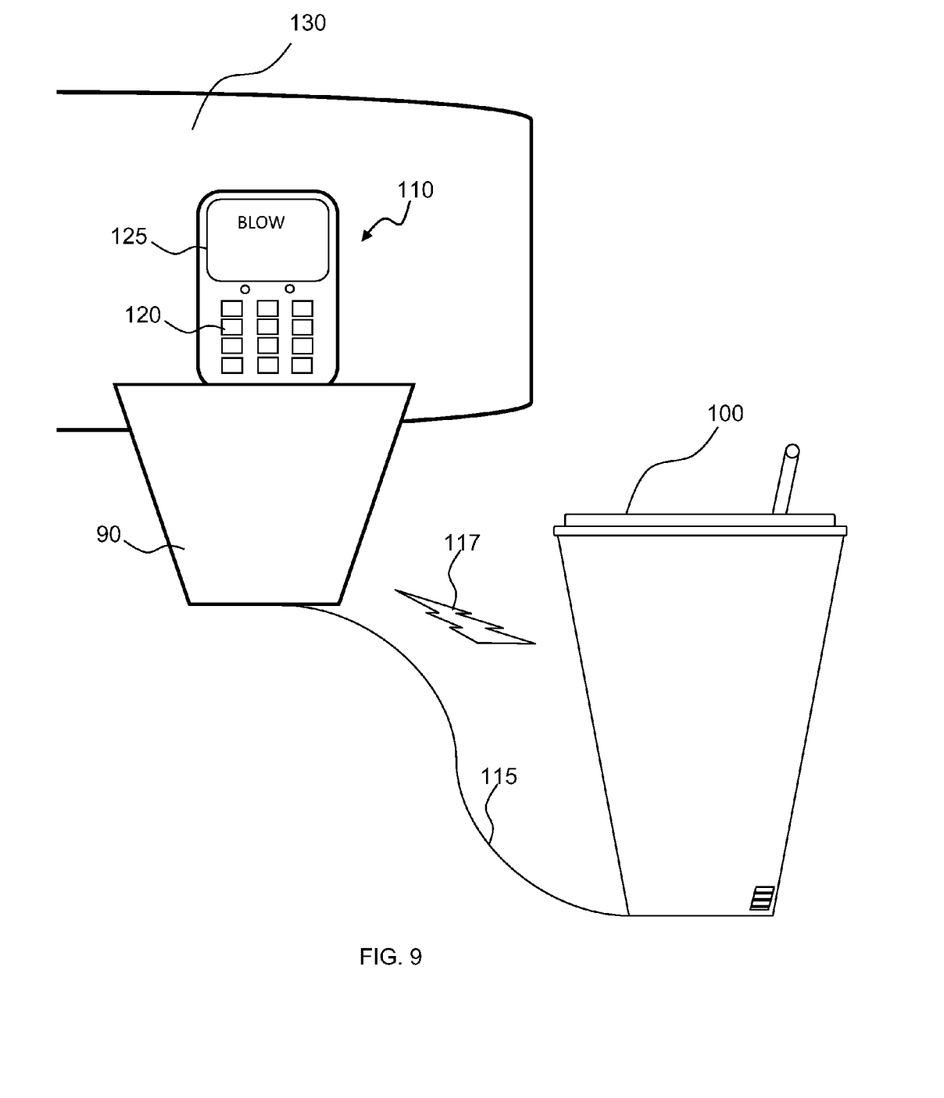
FIG. 9 illustrates a schematic diagram of a IID system wherein a IID housing device communicates either wired or wirelessly with a user interface and display mounted remotely on a vehicle dashboard, in accordance with the disclosed embodiments.

FIG. 9 illustrates a schematic diagram 100 of a IID system wherein a IID beverage housing disguise 110 can communicate either wired 115 or wirelessly 117 with a user interface 110 including keyboard 120 and display 125 mounted remotely on a vehicle dashboard 130. The user interface 110 can also be incorporated with the cup holder 90. It should be appreciated now given the foregoing description that the display 125 and functions keys 120 for a IID system do not have to be integrated directly into the hand held user interface associated with the mouthpiece used to access user breath. Directions and user inputs (other than breath specimen) can be provided on the remote user interface. Such an arrangement can also improve safety during vehicle operation.

Based on the foregoing, it can be appreciated that various embodiments and alternative embodiments can be implemented. For example, in one embodiment a breath alcohol ignition interlock device can comprise a mock beverage housing including at least one of breath alcohol electronics and a hand held breath alcohol analyzer therein; a mouthpiece in fluid communication with an alcohol sensor associated with the at least one of breath alcohol electronics and a hand held breath alcohol analyzer; and a vent exhausting breath from the mock beverage housing. In another embodiment, the mock beverage container housing can be provided in the disguise of at least one of, for example, a coffee cup, a fountain drink cup, a soda can, a soft drink bottle, and so forth, thereby disguising the hand held breath analyzer as a beverage container. In another embodiment, the mouthpiece can be provided in the disguise of at least one of: a coffee cup lid, a fountain drink cup straw, a soda can opening, a soft drink bottle top. In yet another embodiment, the mock beverage container housing accepts and holds therein a hand held interface of a breathalyzer ignition interlock device. In still another embodiment, the mock beverage container housing can be provided in the disguise of at least one of, for example, a coffee cup, a fountain drink cup, a soda can, a soft drink bottle, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top. In other embodiments, the mouthpiece can be in fluid connection with a second mouthpiece associated with said handheld interface of a breathalyzer ignition interlock device. In still other embodiments, the exhaust allows analyzed breath exiting the hand held interface of a breathalyzer ignition interlock interface to exit. In still other embodiments, the mouthpiece can be in fluid connection with a second mouthpiece associated with said handheld interface of a breathalyzer ignition interlock device. In another embodiment, the exhaust allows analyzed breath exiting the hand held interface of a breathalyzer ignition interlock interface to exit. In another embodiment, a wireless communication module can support communication with a base station installed within a motor vehicle. In still another embodiment, the wireless communication module can comprise a Bluetooth wireless communications module. In still further embodiments, the Bluetooth wireless communications module can support data synchronization and communications with said base station.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A breath alcohol ignition interlock device, comprising:
   a mock beverage housing including at least one of breath alcohol electronics and a hand held breath alcohol analyzer therein;
   a mouthpiece in fluid communication with an alcohol sensor associated with the at least one of breath alcohol electronics and a hand held breath alcohol analyzer; and
   a vent exhausting breath from the mock beverage housing.

2. The breath alcohol ignition interlock device of claim 1, wherein said mock beverage container housing is provided in the disguise of at least one of: a coffee cup, a fountain drink cup, a soda can, a soft drink bottle, thereby disguising the hand held breath analyzer as a beverage container.

3. The breath alcohol ignition interlock device of claim 1, wherein said mouthpiece is provided in the disguise of at least one of: a coffee cup lid, a fountain drink cup straw, a soda can opening, a soft drink bottle top.

4. The breath alcohol ignition interlock device of claim 1, wherein said mock beverage container housing accepts and holds therein a hand held interface of a breathalyzer ignition interlock device.

5. The breath alcohol ignition interlock device of claim 4, wherein said mock beverage container housing is provided in the disguise of at least one of: a coffee cup, a fountain drink cup, a soda can, a soft drink bottle, thereby disguising the hand held breath analyzer as a beverage container.

6. The breath alcohol ignition interlock device of claim 4, wherein said mouthpiece is provided in the disguise of at least one of: a coffee cup lid, a fountain drink cup straw, a soda can opening, a soft drink bottle top.

7. The breath alcohol ignition interlock device of claim 4, wherein the mouthpiece is in fluid connection with a second mouthpiece associated with said handheld interface of a breathalyzer ignition interlock device.

8. The breath alcohol ignition interlock device of claim 4, wherein said exhaust allows analyzed breath exiting the hand held interface of a breathalyzer ignition interlock interface to exit.

9. The breath alcohol ignition interlock device of claim 7, wherein the mouthpiece is in fluid connection with a second mouthpiece associated with said handheld interface of a breathalyzer ignition interlock device.

10. The breath alcohol ignition interlock device of claim 9, wherein said exhaust allows analyzed breath exiting the hand held interface of a breathalyzer ignition interlock interface to exit.

11. The breath alcohol ignition interlock device of claim 9, further comprising wireless communication module supporting communication with a base station installed within a motor vehicle.

12. The breath alcohol ignition interlock device of claim 9, wherein said wireless communication module comprises a Bluetooth wireless communications module.

13. The breath alcohol ignition interlock device of claim 12, wherein said Bluetooth wireless communications module supports data synchronization and communications with said base station.

14. The breath alcohol ignition interlock device of claim 11, wherein said Bluetooth wireless communications module supports data synchronization and communications with said base station.

* * * * *